United States Patent
Cross

(10) Patent No.: US 10,467,381 B2
(45) Date of Patent: Nov. 5, 2019

(54) AUTOMATIC DOCUMENTATION OF PATIENT INTAKE AND OUTPUT EVENTS IN A COMPUTERIZED HEALTHCARE ENVIRONMENT

(75) Inventor: Lori N. Cross, Kansas City, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 2924 days.

(21) Appl. No.: 11/422,907

(22) Filed: Jun. 8, 2006

(65) Prior Publication Data
US 2007/0288171 A1    Dec. 13, 2007

(51) Int. Cl.
*G06F 19/00*    (2018.01)
*G16H 10/60*    (2018.01)

(52) U.S. Cl.
CPC .................. *G06F 19/3456* (2013.01)

(58) Field of Classification Search
CPC ........ G06Q 10/00; G06Q 50/00; G16H 10/00; G16H 10/40; G16H 15/00; G16H 20/00; G16H 20/10; G16H 20/13; G16H 20/17; G16H 30/00; G16H 40/00; G16H 50/00; G16H 70/00; G16H 80/00
USPC .................................................. 705/2, 3, 20
See application file for complete search history.

(56) References Cited

U.S. PATENT DOCUMENTS

| | | | |
|---|---|---|---|
| 2002/0132214 A1* | 9/2002 | Mattson et al. | 434/323 |
| 2005/0125256 A1* | 6/2005 | Schoenberg et al. | 705/2 |
| 2006/0253016 A1* | 11/2006 | Baker et al. | 600/410 |

* cited by examiner

*Primary Examiner* — Robert W Morgan
*Assistant Examiner* — Charles P Coleman
(74) *Attorney, Agent, or Firm* — Shook, Hardy & Bacon, LLP

(57) ABSTRACT

The present invention relates to computerized methods and systems for automatically documenting fluid intake and output events for a patient. In one method, a fluid balance event is extracted, an impact value associated with the fluid balance event is received, and a database is populated with the fluid balance event and associated impact value. In another method, a clinical event is received and analyzed to determine whether the event has an impact on the patient's overall fluid balance. If the event is determined to have an impact on the fluid balance, the event is managed as a fluid balance event and an impact value is received for the event. A fluid balance is then updated for the patient using the received impact value.

23 Claims, 8 Drawing Sheets

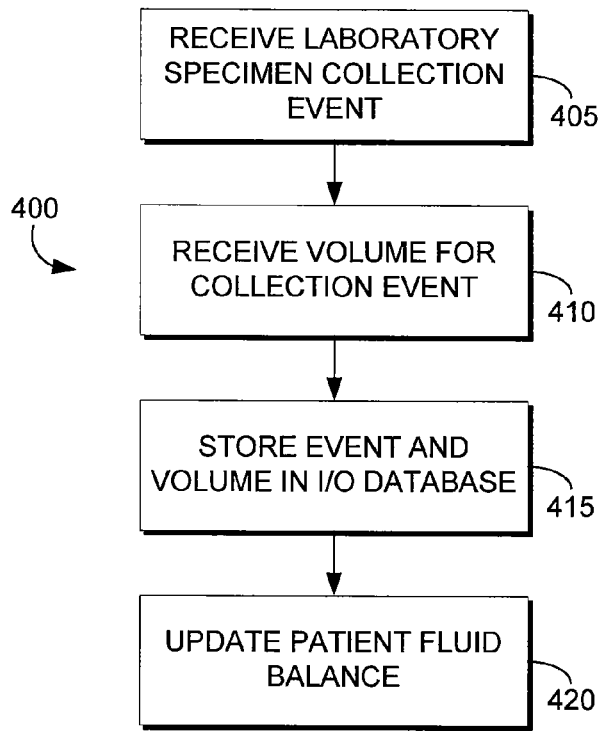
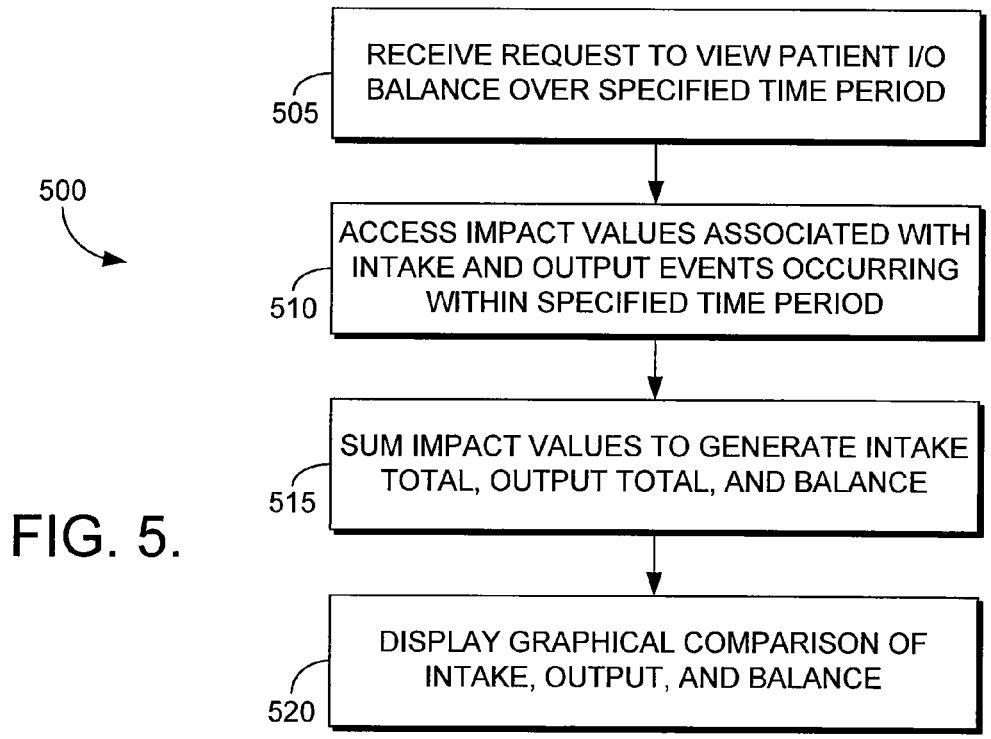

FLUID BALANCE

SATURDAY, NOVEMBER 25, 2006 12:00 AM – SATURDAY, DECEMBER 02, 2006 11:59 PM (CLINICAL RANGE)

| | | 12/1/2006 | 12/1/2006 | GRAND TOTAL |
|---|---|---|---|---|
| INTAKE | ORAL | 350.00 | | 350.00 |
| | IVS | | 1,000.00 | 1,000.00 |
| | ORAL INTAKE | | | |
| | SODIUM CHLORIDE 0.9% | | | |
| | TOTAL | 0.00 | 1,000.00 | 1,000.00 |
| OUTPUT | URINE OUTPUT | 425.00 | 0.00 | 425.00 |
| | URINE VOIDED | | | |
| | TOTAL | 425.00 | 0.00 | 425.00 |
| | BALANCE | -425.00 | 1,000.00 | 575.00 |

SUMMARY

□ INTAKE
□ OUTPUT
□ BALANCE

FIG. 8.

| C | PATIENT | ACCESSION | CONTAINER | ORDER | VOLUME | STATUS | REC DATE | REC TIME | COLL DATE | COLL TIME | COLL ID | PRIORITY |
|---|---------|-----------|-----------|-------|--------|--------|----------|----------|-----------|-----------|---------|----------|
| ▼ | CROSSEN, JAMES ARNOLD | 05-350-0027 | | | | | | | | | | |
| ▼ | | | A : 4 ML SST | LYTES | 4 | DISPATCH | 12/16/2005 | 10:15 AM | 12/16/2005 | 10:15 AM | CERLNC | ST |
| ▼ | | | B : 4 ML LAVENDER | CBC | 4 | DISPATCH | 12/16/2005 | 10:15 AM | 12/16/2005 | 10:15 AM | CERLNC | ST |
| ▼ | | | C : 4 ML RED | BLOOD PRODUCT ORDER | 4 | DISPATCH | 12/16/2005 | 10:15 AM | 12/16/2005 | 10:15 AM | CERLNC | ST |
| ▼ | | | | BLOOD TYPE ABO/RH | | DISPATCH | 12/16/2005 | 10:15 AM | 12/16/2005 | 10:15 AM | CERLNC | ST |
| ▼ | | | | ANTIBODY SCREEN | | DISPATCH | 12/16/2005 | 10:15 AM | 12/16/2005 | 10:15 AM | CERLNC | ST |
| ▼ | | | | CROSSMATCH, IS | | | | | | | | |
| ▼ | | | D : 100 ML URINE CUP | URINALYSIS | 100 | DISPATCH | 12/16/2005 | 10:15 AM | 12/16/2005 | 10:15 AM | CERLNC | ST |

FIG. 9.

AUTOMATIC DOCUMENTATION OF PATIENT INTAKE AND OUTPUT EVENTS IN A COMPUTERIZED HEALTHCARE ENVIRONMENT

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

In an inpatient environment, a patient's fluid balance must be carefully monitored by care-providers. A multitude of health problems, ranging from mild to severe, can arise from either extracellular fluid depletion or extracellular fluid overload. Fluid depletion can result in a variety of problems, such as dizziness, anxiety, confusion, decreased consciousness, weight loss, dry mucous membranes, thready pulse, peripheral vasoconstriction, decreased systolic pressure, increased respiration rate, and a host of other problems. Fluid overload can result in many of the same problems, as well as dependent oedema, pulmonary oedema, abdominal ascites, hepatomegaly, weight gain, raised jugular venous pressure, third heart sound, dyspnoea, ortopnoea, and other problems. Even severe medical problems such as heart attacks or strokes can result from improper fluid balance.

One way of monitoring a patient's fluid balance is to monitor a patient's intake and output (I/O). Currently, I/O documentation is performed manually. For each intake and output event, a healthcare professional must record the volume as well as the type of event. Examples of intake and output events include administration of intravenous fluids, laboratory sample collections, urination, eating, and drinking. Even in computerized healthcare environments, healthcare professionals manually input the I/O data into an I/O balance portion of a patient's electronic medical record. This manual documentation process can lead to errors in the patient's I/O from omitted I/O events or inaccurate data entry.

A particular problem caused by the current manual I/O documentation process results from various departments conducting procedures on a patient that impact the patient's I/O, but failing to document the procedures in the patient's I/O balance. Particular procedures such as the collection of blood samples and urine samples may involve relatively small quantities individually, but can result in large changes in a patient's I/O when added together and considered as a whole. These laboratory procedures, because of their small volumes, are frequently not documented in the patient's I/O. Additionally, administration of radiology contrast media by radiology departments is also often not documented in the patient's I/O. Contrast media quantities administered can often be as high as 500 mL, which could have a dramatic impact on the patient's overall fluid balance.

A process of automatically documenting a patient's I/O and including traditionally undocumented I/O events, such as laboratory procedures and radiological procedures, which would not rely on manual entry, is needed.

SUMMARY

In one embodiment, a method for automatically documenting a fluid balance event for a patient in a computerized environment is provided. A fluid balance event is received, an impact value associated with the event is received, and a database is automatically populated with the fluid balance data. A fluid balance counter corresponding to a specified time period, such as a shift or a day, can be used to monitor the net fluid intake, net fluid output, or overall fluid balance for a patient.

In another embodiment, a system for automatically documenting a fluid balance event for a patient is provided. The system includes a receiving component for receiving fluid balance events and associated impact values, a storage component for storing the fluid balance events and associated impact values, and a display component for displaying fluid balance events and a graphical comparison of fluid intake and output for a patient.

In still another embodiment, a method in a computerized environment for automatically documenting the fluid balance impact of a clinical event is provided. The method receives a clinical event, determines whether the clinical event is a fluid balance event to be documented, and if so, receiving an impact value for the event and updating a fluid balance database with the event and associated impact value.

BRIEF DESCRIPTION OF THE SEVERAL VIEWS OF THE DRAWINGS

The present invention is described in detail below with reference to the attached drawing figures, wherein:

FIG. 4 is a flow diagram illustrating a method for automatically documenting the fluid balance impact of a laboratory specimen collection event;

FIG. 5 is a flow diagram illustrating a method for displaying fluid intake/output data over a specified time period for a patient;

FIG. 6 is an exemplary screen for displaying fluid intake/output data for a patient;

FIG. 7 is an exemplary screen displaying fluid intake/output data for a patient and a graphical comparison of the data;

FIG. 8 is an exemplary screen displaying a user interface for receiving laboratory specimen collection events; and FIG. 9 is an exemplary screen displaying a user interface for documenting radiology clinical events and receiving associated fluid balance impact values.

DETAILED DESCRIPTION

Embodiments of the present invention are directed to systems and methods for automatic documentation of patient intake and output events in a computerized healthcare environment. The present invention allows for the fluid balance impact of various clinical events to be automatically documented for a clinical patient so as to avoid omission of these events, such as can occur with a manual fluid balance documentation process. Other embodiments of the present invention specifically provide for automatic documentation of fluid intake and output in settings such as a radiology environment or laboratory environment, where fluid balance is typically not documented today. Embodiments of the present invention also provide for the graphical representation of these automatically documented events.

Having briefly provided an overview of the present invention, embodiments of the invention will be discussed with reference to FIGS. 1-9.

Figure 1:
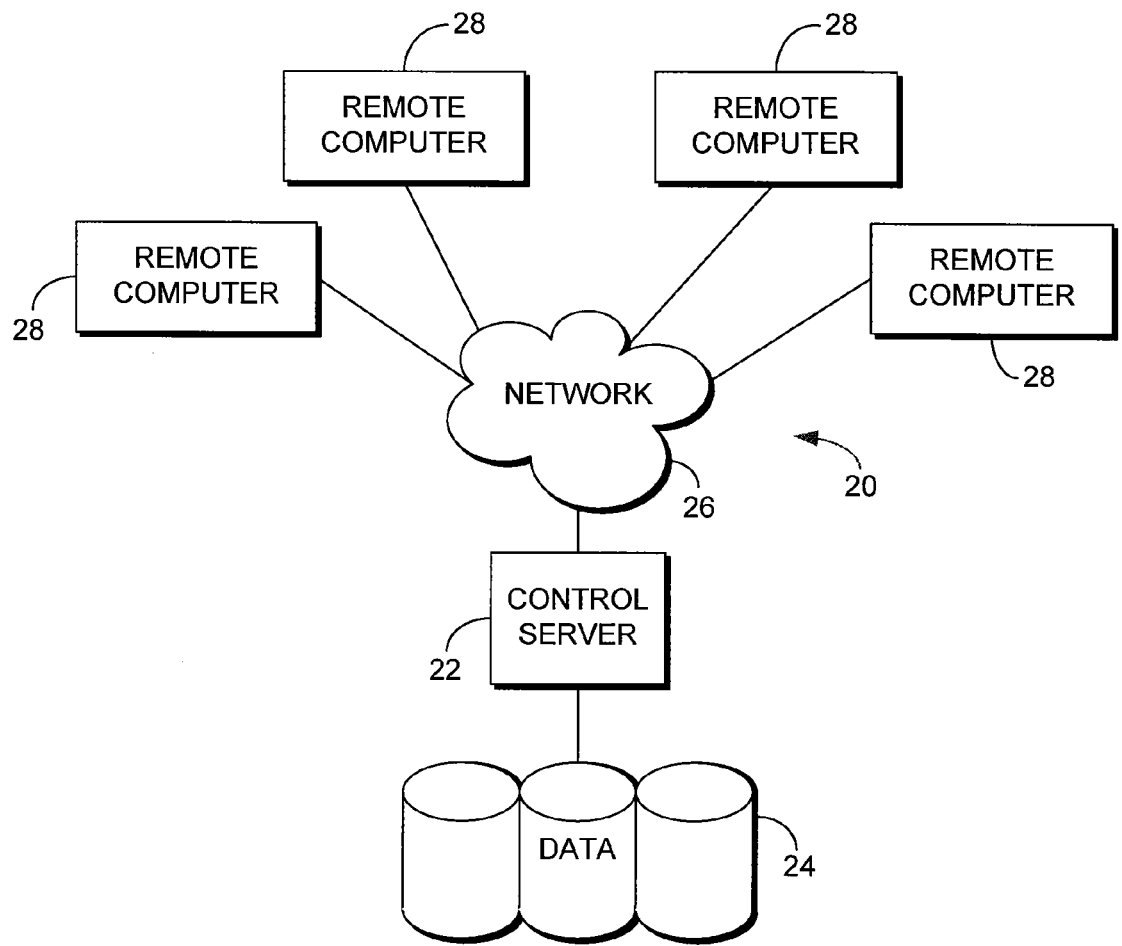
FIG. 1 is a block diagram of an operating environment for use with an embodiment of the present invention.

With reference to FIG. 1, an exemplary medical information system for implementing embodiments of the invention includes a general purpose-computing device in the form of server 22. Components of server 22 may include, but are not limited to, a processing unit, internal system memory, and a suitable system bus for coupling various system components, including database cluster 24 to the control server 22. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 22 typically includes therein or has access to a variety of computer readable media, for instance, database cluster 24. Database cluster 24 can store fluid balance events and associated fluid balance impact values for a clinical patient. Time and date stamps, event details, identification information, and other data associated with these fluid balance events can also be stored in database cluster 24. These fluid balance events can be, for example, fluid intake events and fluid output events. Fluid intake events, by way of example and not limitation, can be oral intake, enteral tube intake, gastric tube intake, blood transfusions, injections, such as injections of radiological contrast media, and other forms of fluid intake events. Fluid output events, by way of example and not limitation, can be urine output, urine samples, drawn blood samples received by a laboratory, and other forms of fluid output events. Associated impact values can be, for example, volumes, masses, weights, flow rates, densities, concentrations and other physical quantities associated with fluid intake and output. In one embodiment, a volume is associated with each fluid balance event.

The fluid balance events stored in database cluster 24 can be standard fluid balance events, which have standard associated impact values that are also stored in database cluster 24. For example, packed red blood cells (PRBCs) may come in standard 125 mL bags. Thus, a standard fluid balance event of transfusion of one 125 mL bag of PRBCs can have an associated standard impact value of 125 mL of fluid intake.

Computer readable media can be any available media that can be accessed by server 22, and includes both volatile and nonvolatile media, removable and non-removable media. By way of example, and not limitation, computer readable media may comprise computer storage media and communication media. Computer storage media includes volatile and nonvolatile, removable and non-removable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 22. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 24, discussed above and illustrated in FIG. 1, provide storage of computer readable instructions, data structures, program modules, and other data for server 22.

Server 22 may operate in a computer network 26 using logical connections to one or more remote computers 28. Remote computers 28 can be located at a variety of locations in a medical or research environment, for example, but not limited to, clinical laboratories, hospitals, other inpatient settings, a clinician's office, ambulatory settings, medical billing and financial offices, hospital administration, veterinary environment and home health care environment. Clinicians include, but are not limited to, the treating physician, specialists such as surgeons, radiologists and cardiologists, emergency medical technologists, discharge planners, care planners, physician's assistants, nurse practitioners, nurses, nurse's aides, pharmacists, dieticians, phlebotomists, microbiologists, laboratory experts, laboratory scientists, laboratory technologists, radiology technicians, genetic counselors, researchers, veterinarians and the like. The remote computers may also be physically located in non-traditional medical care environments so that the entire healthcare community is capable of integration on the network. Remote computers 28 may be a personal computer, server, router, a network PC, a peer device, other common network node or the like, and may include some or all of the elements described above relative to server 22. Computer network 26 may be a local area network (LAN) and/or a wide area network (WAN), but may also include other networks. Such networking environments are commonplace in offices, enterprise-wide computer networks, intranets and the Internet. When utilized in a WAN networking environment, server 22 may include a modem or other means for establishing communications over the WAN, such as the Internet. In a networked environment, program modules or portions thereof may be stored in server 22, or database cluster 24, or on any of the remote computers 28. For example, and not limitation, various application programs may reside on the memory associated with any one or all of remote computers 28. It will be appreciated that the network connections shown are exemplary and other means of establishing a communications link between the computers may be used.

A user may enter commands and information into server 22 or convey the commands and information to the server 22 via remote computers 28 through input devices, such as keyboards, pointing devices, commonly referred to as a mouse, trackball, or touch pad. Other input devices may include a microphone, scanner, or the like. Server 22 and/or remote computers 28 may have any sort of display device, for instance, a monitor. In addition to a monitor, server 22 and/or computers 28 may also include other peripheral output devices, such as speakers and printers.

Although many other internal components of server 22 and computers 28 are not shown, those of ordinary skill in the art will appreciate that such components and their interconnection are well known. Accordingly, additional details concerning the internal construction of server 22 and computer 28 need not be disclosed in connection with the present invention. Although the method and system are described as being implemented in a LAN operating system, one skilled in the art would recognize that the method and system can be implemented in any system.

Figure 2:
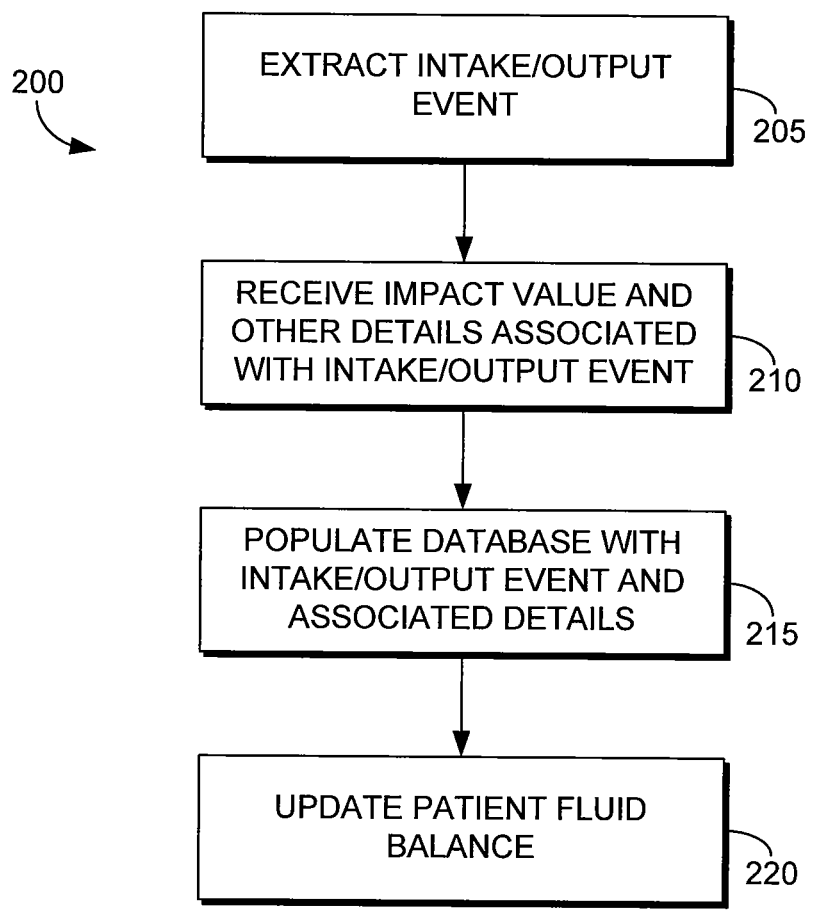
FIG. 2 is a flow diagram illustrating a method for automatic documentation of a fluid balance event for a patient.

With reference to FIG. 2, an exemplary method 200 for automatically documenting a fluid balance event for a patient is shown. The method 200 can be performed in an exemplary computing environment, such as that discussed above with reference to FIG. 1. At a step 205, a fluid balance event, such as a fluid intake or fluid output event, is extracted for a patient from clinical documentation for the patient. This event can be any event that has an impact on the patient's overall fluid balance. A patient's overall fluid balance is a measure of the net fluid intake by a patient and can be a positive value or a negative value depending on whether the patient has had a net fluid gain or a net fluid loss over a specified time period. In an inpatient setting, fluid intake events can be, by way of example and not limitation, administration of intravenous fluids, eating or drinking, consumption of radiological contrast media, blood transfusions, receipt of medication, injections, enteral tube intake, gastric tube intake, or other forms of fluid intake. Fluid output events can be, by way of example and not limitation, urine output, perspiration, oral or nasal discharge, urine laboratory samples, stool laboratory samples, blood samples, vomiting, or other forms of fluid output.

The fluid balance event is extracted from documentation of a clinical event that has an impact on the patient's overall fluid balance. Upon occurrence of a fluid intake or output event, its fluid balance impact is automatically documented while the clinician is charting another activity, such as a radiological or laboratory activity, in clinical event documentation, such as a clinical event table, form, or database. The clinician does not have to manually chart the fluid balance impact of the event in a fluid balance table. Rather, the fluid balance event is automatically extracted or exported when the clinician manually charts a clinical activity or event. The clinical event documentation is independent of the patient's fluid balance documentation, or, in other words, the clinical event documentation is non-fluid-balance-documentation. If the clinical event documentation is in the form of a clinical event table, form or database, then it is a non-fluid-balance-table, non-fluid-balance-form, or a non-fluid-balance database. For example, a phlebotomist may be documenting collection of a blood sample in a laboratory environment. As the clinical event of blood collection is being charted by the phlebotomist, the fluid balance event is extracted from the laboratory clinical event documentation automatically without the phlebotomist having to chart it as a fluid output event in an I/O table. The laboratory clinical event documentation is an example of non-fluid-balance-documentation. The relevant fluid balance event is extracted from the laboratory documentation. Continuing the example, when the phlebotomist charts information associated with the blood collection event in a laboratory clinical event table, form, or database, the system automatically extracts the fluid balance event from this clinical documentation.

At a step 210, an impact value and other details associated with the intake or output event are received. An impact value indicates the magnitude of influence that a particular intake or output event will have on a patient's overall fluid balance. Impact values can be, for example, volumes, masses, weights, flow rates, densities, concentrations and other physical quantities associated with fluid intake and output. Details associated with the intake/output event can be information such as the date and time of the event, the type of event, patient identification information, comments by the healthcare professional, and other information relevant to the event. For example, a radiology technician may record that a patient was administered 800 mL of a radiology contrast media on Dec. 16, 2006 at 10:25 A.M. while entering clinical event documentation for completion of a radiology order. In this case, an impact value of 800 mL associated with this intake event would be automatically received in the background without the radiologist manually charting the fluid balance impact directly in the patient's fluid balance documentation, such as an I/O table.

At a step 215, a fluid balance database is automatically populated with the fluid balance event, the impact value, and the associated details. This information can be stored locally or remotely. The database can store all fluid intake and output events, as well as their associated impact values and other details. The information stored in the database has assigned time and date stamps designating when the particular event occurred. This facilitates organization of fluid balance data by time period, such as by shift, day, week, visit, or by any other time frame. The fluid balance data can be filtered to allow a healthcare professional to access shift totals, daily totals, weekly totals, or totals for any other desired time period for a particular patient. The documentation process is automatic and does not rely on a user manually populating the database with intake and output events.

At a step 220, the overall fluid balance for the patient is updated. If the event is a fluid intake event, then the fluid balance is increased by the amount of the impact value. If the event is a fluid output event, the overall fluid balance is decreased by the amount of the impact value. In one embodiment, the overall patient fluid balance is represented using a fluid balance counter. The fluid balance counter designates the net fluid intake or the net fluid output for a patient over a specified time period. The fluid balance counter can be a positive value to designate a net fluid gain or a negative value to designate a net fluid loss. The overall patient fluid balance is updated automatically upon population of the database with the intake or output event. The database can be populated with the intake or output event upon completion of an order, completion of an activity, or can be populated retrospectively. Thus, the point at which the patient fluid balance is updated can depend on when the database is populated. Additionally, the overall patient fluid balance can vary based on the time and date filters applied to the fluid balance data. For example, a patient may have a net fluid loss for a particular day, but may have a net fluid gain for a particular shift within that day.

Upon completion of the exemplary method 200, the fluid balance event, its associated impact value, and other relevant details have been automatically documented. By accessing the overall patient fluid balance, a physician, nurse, or other healthcare professional can determine whether a patient may be at risk for problems associated with fluid depletion or fluid overload. This automatically documented data can be filtered and displayed in various exemplary user interfaces, as will be discussed below.

Figure 3:
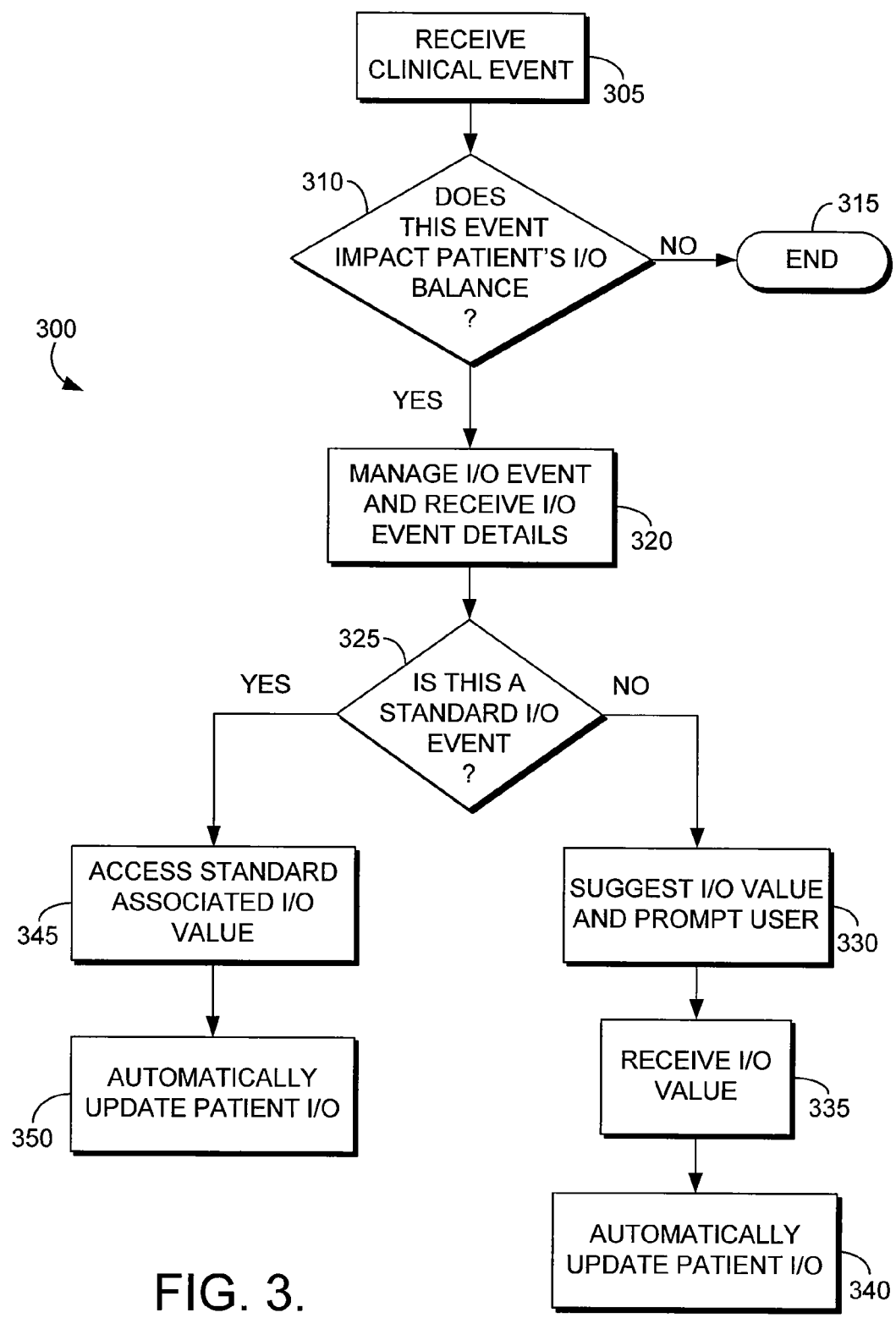
FIG. 3 is a flow diagram illustrating a method for automatically documenting the fluid balance impact of a clinical event.

With reference to FIG. 3, an exemplary method 300 for automatically documenting the fluid balance impact of a clinical event for a patient is shown. At a step 305, a clinical event is received. The clinical event can be any event relevant to treatment of the patient that is entered into an electronic medical record system. The event can be, by way of example and not limitation, a laboratory collection, a radiology event involving contrast media or other medication, administration of fluid from a volume-measuring pump, a nutrition or dietary event, administration of medication, a blood or other fluid transfusion, an excretory event, or any other event that is charted electronically for a patient. At a step 310, the system determines whether the event has an impact on the patient's overall fluid balance. This can be done by comparing the event to a configurable pre-determined database of events defined as having a fluid intake/output effect. If it is determined that the event does not impact the patient's fluid balance, then, at a step 315, the process ends. However, if it is determined that the event does impact the patient's fluid balance, then the process continues to automatically document the fluid balance impact of the event. For example, a blood specimen collection event, which is defined as having a fluid balance impact, may be received in a computerized laboratory environment. In this case, the system determines that a blood specimen collection is a fluid output event and proceeds to automatically document its fluid balance impact.

At a step 320, the event is managed as a fluid balance event and details associated with the event are received. At a step 325, the system determines whether this event is a standard intake/output event. A standard intake/output event is a fluid balance event that has an associated standard impact value. For example, certain events may always have the same volume of intake or volume of output associated with them. Particular laboratory tests may always require drawing a standard quantity of blood or fluid from a patient. This would make these events standard output events. Likewise, certain fluid infusion events may always involve infusion of a standard volume of fluid. This would make these events standard intake events. Standard intake and output events can be defined by a configurable pre-determined database.

If it is determined that the event is not a standard fluid balance event, then at a step 330, an impact value can be suggested and the user can be prompted to input an impact value. For example, an impact value typically associated with events of this type can be suggested. A unit of measurement can also be suggested, such as in a drop-down menu. At a step 335, an impact value associated with the event is received. For example, the user may enter that 100 mL of radiology contrast media was consumed by the patient. The impact value may also be received automatically, such as from an electronic volumetric device. For example, an intravenous (IV) pump capable of measuring the volume of fluid discharged may be coupled to a remote computer. The IV pump may indicate that 200 mL of saline was administered to the patient. In this case, an impact value of 200 mL of fluid intake is received by the system. This can be done without the user manually entering the impact value in the patient's clinical event documentation.

At a step 340, a database is populated with the fluid balance event, the associated impact value, and the details associated with the event, and the overall fluid balance for the patient is automatically updated. The data entered by the user in the clinical event documentation, such as the clinical event table, form, or database, is used to populate the fluid balance database without the user having to manually enter the fluid balance data into fluid balance documentation, such as a fluid intake/output table, form, or database.

If it is determined that the event is a standard fluid balance event, then at a step 345, a standard impact value associated with the event is accessed. The standard impact value can be accessed from a configurable pre-determined database. At a step 350, the fluid balance event, standard impact value, and the details associated with the event are placed into a fluid balance database and the patient's overall fluid balance is automatically updated.

For example, a patient may be infused with a bag of packed red blood cells (PRBCs), which may come in standardized 125 mL bags. When this clinical event is charted, the system determines that this event impacts the patient's overall fluid balance. As a result, the event is managed as an intake/output event. Additionally, the system determines that this is a standard intake/output event with an associated standard impact value of 125 mL. The database containing the overall fluid balance information for the patient is updated with the PRBCs infusion event and its associated standard impact value of 125 mL. This impact value is then automatically added to the fluid balance counter for this specified time period. The fluid balance counter may vary depending on the specified time period. For example, the counter may be a positive value designating a net fluid gain for one shift but may be a negative value designating a net fluid loss for another shift. A time and date stamp associated with each fluid balance event is used to determine whether to use the fluid balance event in determining the overall fluid balance for a specified time period.

With reference to FIG. 4, a method 400 for automatically documenting the fluid balance impact of a laboratory specimen collection event is shown. Often, laboratory specimen collections are not documented in a patient's fluid balance information today. This method 400 automatically documents the fluid balance impact of a laboratory specimen collection event while a user is entering clinical event documentation for the laboratory event in a computerized laboratory environment, without the user having to document the fluid balance impact in I/O documentation, such as an I/O table, manually. At a step 405, a laboratory specimen collection event is received. For example, a nurse may be logging receipt of a 100 mL urine sample for purposes of a urinalysis test. If this specimen collection is defined as having an impact on the patient's overall fluid balance, the event is automatically documented as a fluid balance event. In this case, the specimen collection would be automatically documented as a fluid output event.

At a step 410, a volume associated with the collection event is received. Continuing the example from above, a volume of 100 mL for the urine sample is received. The volume of the specimen collection is the fluid balance impact value, in this case. At a step 415, the collection event and its associated volume are stored in the patient's intake/output balance database. This occurs automatically without the user who is logging the specimen entering the volume of the specimen collection into a separate I/O chart. For example, the clinician user may be documenting collection of the specimen in a laboratory collection event table. The volume of the sample collected is received and stored in the laboratory collection table. Additionally, the collection event and volume collected are automatically stored in the patient's I/O balance database without the user having to record this event separately in an I/O chart. At a step 420, the patient's overall fluid balance is updated using the volume. For example, the patient's overall fluid balance is decremented by the volume of fluid collected for the laboratory collection event. An exemplary user interface, such as that shown in FIG. 8 and discussed below, can be used to log specimen collections, which are received as fluid balance events and stored in the patient's intake/output database. The method 400 links laboratory activities with a patient's overall fluid balance to ensure accurate documentation of fluid intake and output.

With reference to FIG. 5, a method 500 for displaying automatically documented fluid balance data for a patient for a specified time period is shown. At a step 505, a request is received to view a patient's fluid balance data for a specified time period. For example, a nurse may wish to view a patient's fluid balance from a previous shift, from a previous day, or for a current shift. At a step 510, the impact values for the patient that are associated with fluid balance events occurring within the specified time period are accessed. Time and date stamps associated with each of the events are used to identify the events occurring within the requested specified time period. At a step 515, the impact values associated with these identified events are accessed and summed to generate a fluid intake total, a fluid output total, and a fluid balance total for the specified time period. At a step 520, a graphical representation of the data is displayed. The graphical representation allows for the fluid intake total, fluid output total, and fluid balance total to be compared and analyzed. An exemplary user interface for displaying this graphical representation is discussed below.

Figure 6:
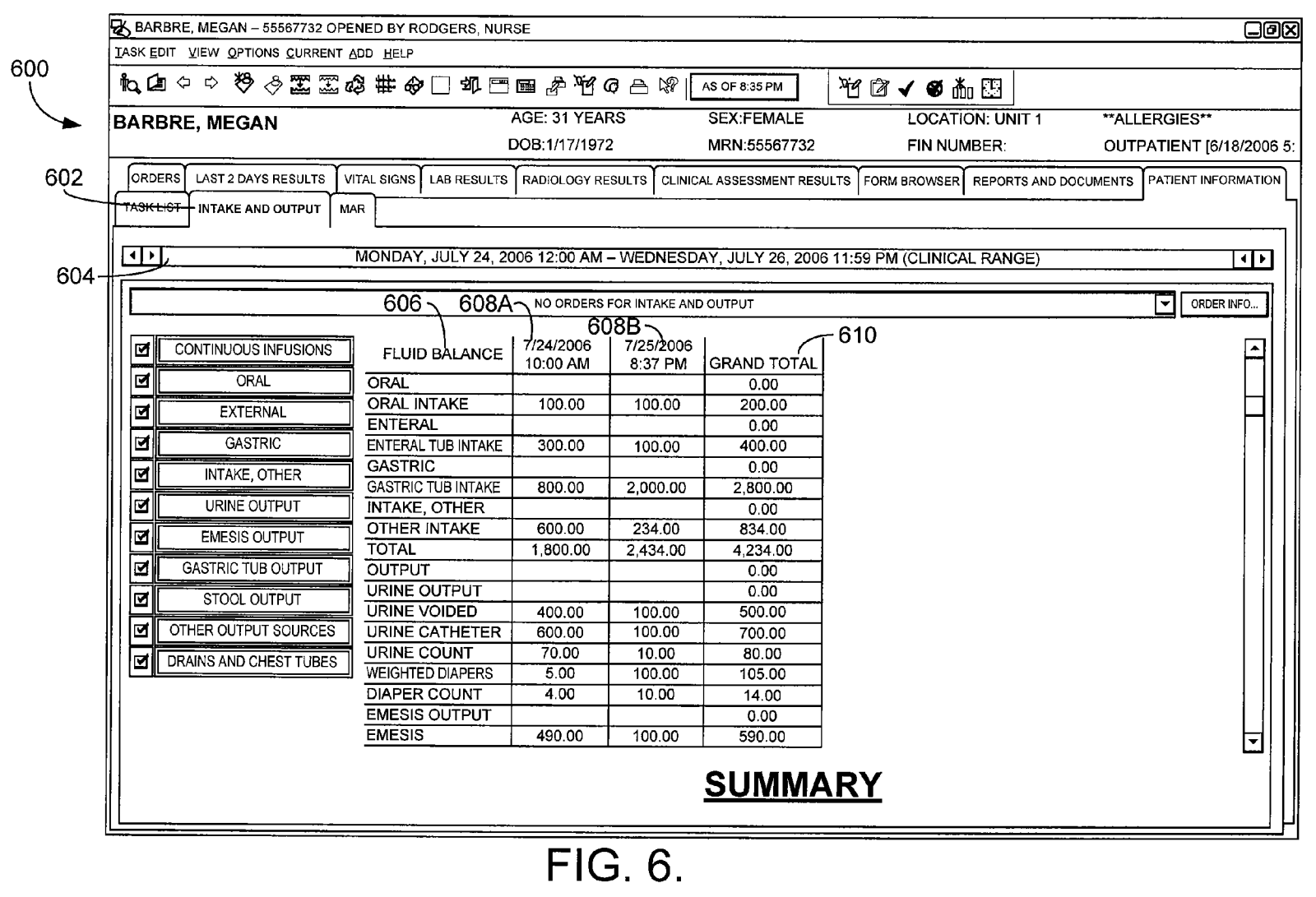

With reference to FIG. 6, an exemplary user interface 600 for displaying fluid balance documentation for a patient for a specified time period is shown. In this embodiment, the data is displayed in an intake and output tab 602. The tab 602 displays the specified time period used to filter the fluid balance data in a time and date region 604. For example, the region 604 indicates that fluid intake and output data for the patient is shown for the days Monday through Wednesday, July 24 through July 26. The user interface 600 contains an intake and output table with a fluid balance category column 606, fluid balance event columns 608A-B and a total column 610. The category column 606 indicates the category of fluid balance event. Columns 608A and 608B contain impact values associated with fluid intake and output events occurring at specified times. The total column 610 displays fluid balance totals.

As shown in FIG. 7, a user interface 700 for displaying fluid balance documentation for a patient for a specified time period is shown. The intake total 702 displays the sum of all fluid intake impact values for fluid intake events occurring in the specified time period. The output total 704 displays the total fluid output impact values for fluid output events occurring in the specified time period. The fluid balance counter 706 displays the overall fluid balance for the patient for the specified time period. For example, the fluid balance counter 706 displays that the patient has a net fluid gain of 575 mL for the period of November 25 through December 2.

User interface 700 can also contain a graphical comparison 708 of the fluid intake total 710, the fluid output total 712, and the overall fluid balance 714 for the specified time period. Legend identifiers 716, 718, and 720 correspond to the graphical depictions of the intake total 710, output total 712, and overall fluid balance total 714, respectively.

With reference to FIG. 8, a user interface 800 for receiving clinical event documentation for laboratory specimen collection events is shown. The user interface 800 is operative to receive specimen collection events and associated volumes in a clinical event table 801 to be extracted and stored in a patient's fluid balance database. The user interface 800 includes a container column 802 displaying specimen collection events 806, 808, 810, and 812. An associated volume column 804 contains volume impact values 814, 816, 818, and 820, which are associated with collection events 806, 808, 810, and 812, respectively. As the user logs specimen collection events using user interface 800, the exemplary method 400 automatically documents the fluid balance impact of the received specimen collection events. In most healthcare laboratory environments today, the fluid balance impact of laboratory specimen collection events is not documented in the patient's overall fluid balance. This process 400 ensures automatic inclusion of the specimen collection events in the patient's overall fluid balance.

Figure 9:
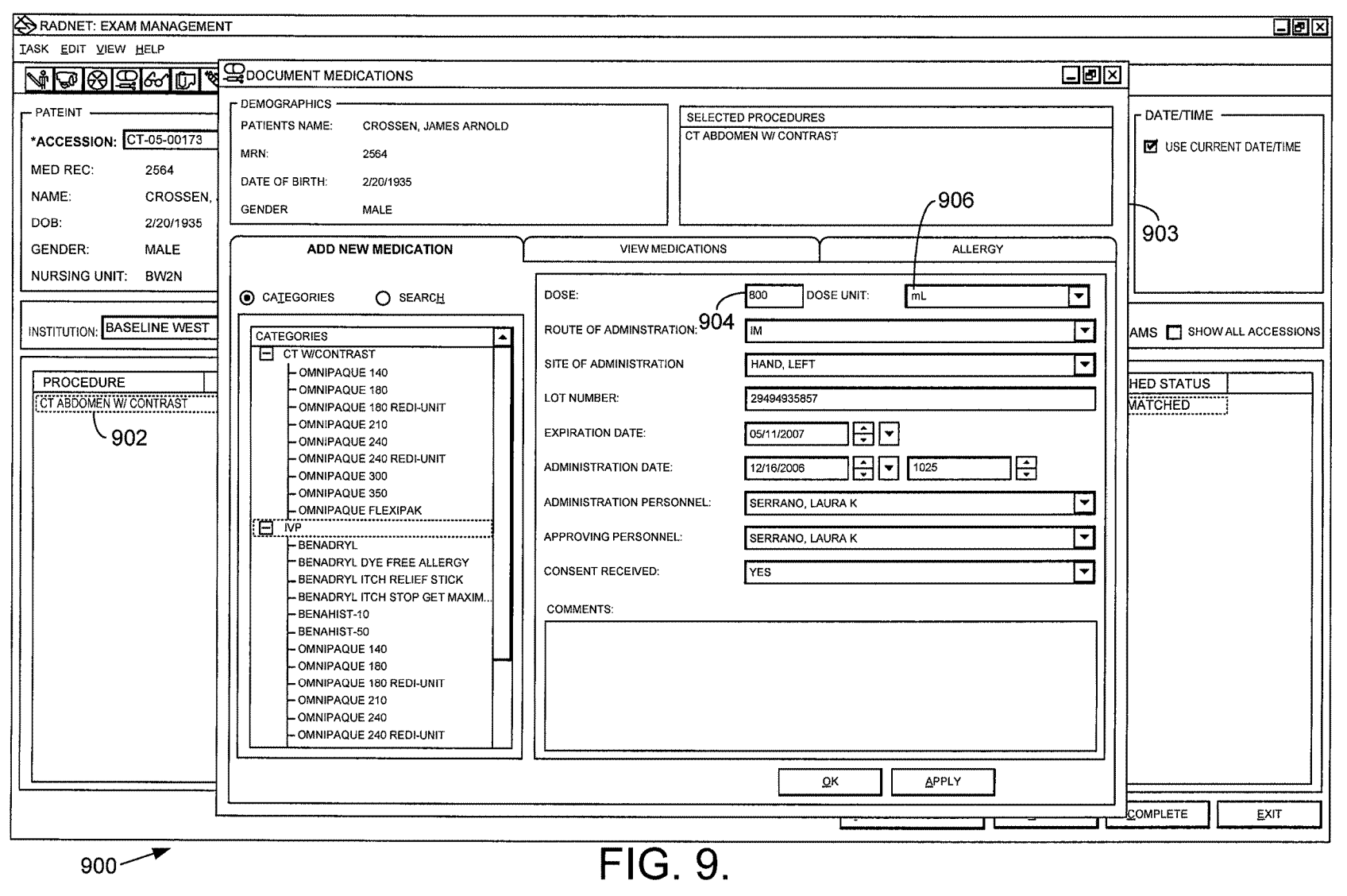

With reference to FIG. 9, a user interface 900 for receiving clinical event documentation for radiology events is shown. Fluid balance events and associated fluid balance impact values to be automatically documented can be extracted from this documentation. For example, a radiological technician may be completing a CT scan of a patient's abdomen and administering contrast media to a patient. While documenting the radiology order 902, the technician can enter a dose for the contrast media administered in a clinical event form 903. A dose region 904 is operative to receive a numerical quantity corresponding to the impact value and a dose unit region 906 is operative to receive a unit of measurement for the particular physical quantity associated with the dosage of contrast media. In this case, user interface 900 is used to receive an impact value of 800 mL associated with a fluid intake event of administration of radiology contrast media. In this example, while a technician is documenting performance of the radiology procedure in the clinical event documentation, the exemplary method 300 determines that the clinical event impacts the patient's fluid balance and manages the event accordingly to automatically document the fluid balance impact of the event in the patient's overall fluid balance. Today, fluid intake associated with consumption of contrast media in a radiology department is often not documented in a patient's overall fluid balance. This process 300 ensures automatic inclusion of radiology intake events such as this in the patient's overall fluid balance.

Clinical events, such as the laboratory specimen collections and radiological procedures discussed above, which have been automatically documented in the patient's overall fluid balance can be displayed in user interfaces, such as those discussed above with reference to FIG. 6 and FIG. 7, using the exemplary method 500 discussed above.

The present invention has been described in relation to particular embodiments, which are intended in all respects to illustrate rather than restrict. Alternative embodiments will become apparent to those skilled in the art that do not depart from its scope. Many alternative embodiments exist, but are not included because of the nature of this invention. A skilled programmer may develop alternative means for implementing the aforementioned improvements without departing from the scope of the present invention.

It will be understood that certain features and sub-combinations of utility may be employed without reference to features and sub-combinations and are contemplated within the scope of the claims. Furthermore, the steps performed need not be performed in the order described.

The invention claimed is:

1. One or more computer-readable media having computer-executable instructions embodied thereon for causing a computing device to perform a method for automatically documenting a fluid balance event for a patient, the method comprising:

receiving a signal indicating that a fluid balance event associated with an impact value impacts a patient's overall fluid balance, wherein the impact value is a physical quantity associated with fluid intake and output, and wherein the overall fluid balance is a numerical measure of the net fluid intake of the patient;

automatically and without user interaction extracting the fluid balance event for a patient from clinical event documentation;

determining the fluid balance event is a standard fluid balance event;

receiving the impact value associated with the fluid balance event that indicates the magnitude of influence that a particular fluid balance event has on a patient's overall fluid balance, wherein the impact value is a standard impact value received from a first database;

automatically and without user interaction populating a second database with the fluid balance event and the impact value; and automatically and without user interaction updating an overall fluid balance for the patient utilizing the impact value.

2. The media of claim 1, further comprising:
automatically updating a fluid balance counter using the impact value.

3. The media of claim 1, wherein the fluid balance event is a fluid intake event.

4. The media of claim 1, wherein the fluid balance event is a fluid output event.

5. The media of claim 3, wherein the impact value designates a volume of fluid intake by the patient.

6. The media of claim 2, wherein the fluid balance counter is incremented.

7. The media of claim 4, wherein the impact value designates a volume of fluid output from the patient.

8. The media of claim 2, wherein the fluid balance counter is decremented.

9. The media of claim 1, wherein the second database is populated upon completion of an order or upon performance of an activity.

10. The media of claim 1, wherein the computerized environment is a computerized radiology environment or a computerized laboratory environment.

11. The media of claim 1, wherein the clinical event is a laboratory collection event, a radiology event, or a medication administration event.

12. The media of claim 1, wherein the clinical event documentation is a clinical event table, a clinical event form, or a clinical event database.

13. The media of claim 1, wherein the clinical event documentation is a non-fluid-balance documentation.

14. The media of claim 1, wherein the clinical event documentation is automatically populated using an electronic volume-measuring device.

15. The media of claim 1, further comprising:
displaying a table of fluid balance events and a fluid balance graph summarizing fluid balance events having associated time and date stamps corresponding to a specified time period.

16. One or more computer-readable media having computer-executable instructions embodied thereon for causing a computing device to perform a method for automatically documenting a fluid balance impact of a fluid balance event for a patient, the method comprising:

receiving a signal indicating a clinical event and details associated with the clinical event for a patient;

determining that the clinical event is a standard fluid event having an impact on an overall fluid balance for the patient based on an impact value, wherein the impact value is a physical quantity associated with fluid intake and output, and wherein the overall fluid balance is a numerical measure of the net fluid intake of the patient;

receiving the impact value from a first database, the impact value being a standard impact value associated with the clinical event that indicates the magnitude of influence that the clinical event had on a patient's overall fluid balance; and automatically and without user interaction updating a second database containing data corresponding to the overall fluid balance for the patient using a volume associated with the clinical event.

17. The media of claim 16, wherein the clinical event is a laboratory collection event, a radiology event, or a medication administration event.

18. The media of claim 16, further comprising:
upon receiving a request to view information relevant to the overall fluid balance for the patient, displaying a table summarizing all or a portion of the data corresponding to the overall fluid balance for the patient.

19. The media of claim 16, further comprising:
determining if the clinical event is a fluid intake event;
if the clinical event is a fluid intake event, updating the second database by adding the volume to the overall fluid balance; and
otherwise, updating the second database by subtracting the volume from the overall fluid balance.

20. A computer system for automatically documenting a fluid balance event for a patient, the system comprising:
one or more processors;
one or more databases;
one or more output devices; and
computer-storage memory having computer-executable instructions stored thereon that, when executed by at least one of the one or more processors, configure the computer system to:
receive a fluid balance event for a patient from clinical event documentation, the fluid balance event impacting the patient's overall fluid balance, wherein the overall fluid balance is a numerical measure of the net fluid intake of the patient;
determining that the fluid balance event is a standard fluid balance event;
receiving an impact value associated with the standard fluid balance event from a database, wherein the impact value is used to determine that the standard fluid balance event impacts the patient's overall fluid balance, wherein the impact value is a physical quantity associated with fluid intake and output;
store the standard fluid balance event and the associated impact value;
automatically and without user interaction update the overall fluid balance utilizing the impact value; and
display at least one fluid balance event occurrence and a fluid balance graph summarizing fluid balance events over a time period.

21. The computer system of claim 20, wherein the clinical event is a laboratory collection event, a radiology event, or a medication administration event.

22. The computer system of claim 20, wherein the clinical event documentation is a clinical event table, a clinical event form, or a clinical event database.

23. The system of claim 22, wherein the clinical event table is a non-fluid-balance-table, the clinical event form is a non-fluid-balance-form, and the clinical event database is a non-fluid-balance-database.

* * * * *